(12) United States Patent
Wolf

(10) Patent No.: US 11,648,361 B2
(45) Date of Patent: May 16, 2023

(54) NONINVASIVE VENTILATION HELMET

(71) Applicant: Andrew Wolf, Freeport, NY (US)

(72) Inventor: Andrew Wolf, Freeport, NY (US)

( * ) Notice: Subject to any disclaimer, the term of this patent is extended or adjusted under 35 U.S.C. 154(b) by 0 days.

(21) Appl. No.: 17/214,848

(22) Filed: Mar. 27, 2021

(65) Prior Publication Data

US 2021/0299385 A1   Sep. 30, 2021

Related U.S. Application Data

(60) Provisional application No. 63/013,062, filed on Apr. 21, 2020, provisional application No. 63/001,453, filed on Mar. 29, 2020.

(51) Int. Cl.
| | | |
|---|---|---|
| *A61M 16/06* | (2006.01) | |
| *A61M 16/20* | (2006.01) | |
| *A62B 7/10* | (2006.01) | |

(52) U.S. Cl.
CPC .......... *A61M 16/06* (2013.01); *A61M 16/20* (2013.01); *A61M 2202/0208* (2013.01);
(Continued)

(58) Field of Classification Search
CPC .... A61M 16/06; A61M 16/20; A61M 16/201; A61M 16/208; A61M 16/209; A61M 16/0627; A61M 16/0605; A61M 2202/0208; A41D 13/018; A41D 13/00; Y10S 2/03; A42B 3/0486; A42B 3/288; A42B 3/326; A42B 3/00; A42B 3/04; A42B 3/28; A42B 1/046; A62B 17/00; A62B 17/04; A62B 18/025; A62B 18/00; A62B 18/02; A62B 18/04; A62B 18/084;
(Continued)

(56) References Cited

U.S. PATENT DOCUMENTS 4,236,514 A * 12/1980 Moretti .................. A62B 17/04
128/201.23
4,433,988 A *  2/1984 Hinchliffe .............. A62B 18/04
2/425
(Continued)

FOREIGN PATENT DOCUMENTS

| CN | 102238976 B | 1/2015 |
|---|---|---|
| IT | 20090754 A1 | 11/2010 |
| WO | 2007128571 A2 | 11/2007 |

OTHER PUBLICATIONS

Aurike Savickaite et al., Helmet Based Ventilation (Mar. 29, 2021), https://www.helmetbasedventilation.com/. (4 pages).
(Continued)

*Primary Examiner* — Joseph D. Boecker
*Assistant Examiner* — Brian T Khong
(74) *Attorney, Agent, or Firm* — Phillips Nizer LLP

(57) ABSTRACT

An apparatus for providing a pressurized atmosphere to a patient including one or more flat sheets of plastic arranged in an envelope and sealed around the periphery to form an airtight container. The helmet has an airtight collar that is configured to accommodate a patient's neck and form an airtight seal. An intake port is integrated into the helmet and receives pressurized air. An exhaust port is integrated into the helmet near the patient's mouth when the helmet is in use. Additional ports can be added to the helmet to provide more functionality such as feeding or supplemental oxygen.

19 Claims, 19 Drawing Sheets

US 11,648,361 B2
Page 2

(52) U.S. Cl.
CPC ... *A61M 2205/18* (2013.01); *A61M 2205/581* (2013.01); *A61M 2207/00* (2013.01); *A61M 2230/205* (2013.01)

(58) Field of Classification Search
CPC .. A62B 18/08; A62B 7/12; A62B 7/00; A62B 7/10; A62B 7/02; A62B 7/04; A62B 23/02; A62B 23/00; A62B 23/025; A61G 10/04; B63C 11/06; B63C 11/00; B63C 11/02; B63C 11/04; B63C 11/12; B63C 11/14
See application file for complete search history.

(56) References Cited

U.S. PATENT DOCUMENTS

| | | | | |
|---|---|---|---|---|
| 4,466,432 A * | 8/1984 | Wise | | A62B 17/04 128/201.23 |
| 4,484,575 A * | 11/1984 | Brockway | | A62B 17/04 128/201.23 |
| 4,502,157 A * | 3/1985 | Wong | | A62B 17/04 2/1 |
| 4,552,140 A * | 11/1985 | Cowley | | A62B 17/04 128/201.25 |
| 4,561,162 A * | 12/1985 | Brockway | | A62B 17/04 29/428 |
| 4,619,254 A * | 10/1986 | Moretti | | A62B 17/04 128/201.23 |
| 4,620,538 A * | 11/1986 | Koegel | | A61M 16/0627 128/201.23 |
| 4,805,639 A * | 2/1989 | Dial | | A41D 13/1153 128/857 |
| 4,870,959 A * | 10/1989 | Reisman | | A62B 17/04 128/201.25 |
| 5,113,527 A * | 5/1992 | Robertson-McKenzie | | A62B 17/04 2/7 |
| 5,113,854 A * | 5/1992 | Dosch | | A62B 7/08 128/205.27 |
| 5,133,344 A * | 7/1992 | Jurrius | | A62B 17/04 128/201.23 |
| 5,214,803 A * | 6/1993 | Shichman | | A62B 17/04 2/202 |
| 5,226,409 A * | 7/1993 | Bower | | A62B 17/04 128/201.23 |
| 5,572,880 A * | 11/1996 | Frustaci | | A62B 7/06 128/201.21 |
| 5,697,361 A * | 12/1997 | Smith | | A62B 7/12 128/204.15 |
| 5,819,728 A | 10/1998 | Ritchie | | |
| 6,088,833 A * | 7/2000 | Welchel | | A41D 13/0002 2/457 |
| 6,374,823 B1 * | 4/2002 | Hajianpour | | A62B 17/04 128/201.22 |
| 6,792,623 B2 | 9/2004 | Luppi | | |
| 7,677,245 B2 | 3/2010 | Borsari | | |
| 2003/0075174 A1 * | 4/2003 | Shahaf | | A62B 17/04 128/201.25 |
| 2005/0115566 A1 * | 6/2005 | Van den Akker | | A61M 16/00 128/205.24 |
| 2006/0283455 A1 * | 12/2006 | Walker | | A41D 13/1184 128/206.24 |
| 2009/0004047 A1 * | 1/2009 | Hunter | | A62B 11/00 422/4 |
| 2010/0083958 A1 | 4/2010 | Lloyd et al. | | |
| 2011/0011404 A1 * | 1/2011 | Forbes | | A62B 17/04 128/206.15 |
| 2012/0152241 A1 * | 6/2012 | Pettitt | | A61M 16/0009 128/201.23 |
| 2013/0190796 A1 * | 7/2013 | Tilson | | A61M 25/1029 606/192 |
| 2014/0251332 A1 * | 9/2014 | Martin | | A61M 16/0833 128/203.29 |
| 2017/0072159 A1 * | 3/2017 | Romano | | A61M 16/0057 |

OTHER PUBLICATIONS

Houman Armirfarzan et al., Helmet CPAP: how an unfamiliar respiratory tool is moving into treatment options during COVID-19 in the US. 14:1-3 Therapeutic Advances in Respiratory Disease, Aug. 30, 2020. (3 pages).
Michael Harrison et al., Oxygen therapy via a noninvasive helmet: a COVID-19 novelty with potential post-pandemic uses, Respiratory Med. Case Rep. 32 (2021) 101369, Feb. 21, 2021. (6 pages).
Bhakti Patel et al. Alternatives to Invasive Ventilation in the COVID-19 Pandemic. JAMA. 2020;324(1):43-44. Jun. 4, 2020. (8 pages).
Machine translation of abstract for CN 102238976, p. 1.
Machine translation of description for ITMI20090754, p. 3.

* cited by examiner

NONINVASIVE VENTILATION HELMET

BACKGROUND

COVID-19 affects a patient's lungs and their ability to breathe. Ventilators have proven to be an effective treatment for the effects of the virus. However, current ventilators are invasive and they require the patient to be intubated. This is a complicated, costly, and dangerous procedure for the patient and the medical personnel due to potential exposure to the virus.

Multiple clinical studies have shown the effectiveness of NIV (Noninvasive ventilation) helmets for patients suffering from ARDS (Acute Respiratory Distress Syndrome) and similar serious breathing issues. NIV helmets have been successfully used to treat COVID-19 in Europe, and particularly in Italy where use of these helmets was common in hospitals even before the current outbreak.

A 3-year study at the University of Chicago demonstrated the effectiveness of helmet-based NIV and that it has significant benefits over intubation with a ventilator. Doctors estimate that the use of NIV helmets could decrease the number of people who need to be intubated with a ventilator by 20% or more. Given the expected volume of patients and the scarcity of ventilators, this reduction of patients who need to be intubated is significant.

Previous NIV helmet products have aspects that make them unsuitable for use with the COVID-19 pandemic. For example, prior helmets do not make an airtight seal on the patient's neck. As a result, when NIV forces a high volume of pressurized air into the helmet, unfiltered air leaks out that may contain virus particles or other contaminants leaking out at a high velocity that can fill a volume quickly. This may put caregivers at an unacceptable risk. Other deficiencies of prior helmets include that known products do not allow patients to be tended to (e.g., fed, cleaned) without opening or removing the helmet, which again puts caregivers in danger of escaping virus and other contaminants.

Yet other deficiencies of prior products for NIV treatments including masks are that they are not suitable for long term situations. For example, patients that wear tight fitting masks may develop sores around the seal that require treatment to be discontinued. A mask also makes daily events such as eating drinking and hygiene difficult. As an example, the mask must be removed for the patient to eat, brush their teeth. Each event that requires the removal of the mask, creates an event where the patient is exposed to lower pressure for a period of time and may expose those in the area to a contagious disease.

Yet further deficiencies with previous products are that they are designed for use exclusively with a ventilator as the air supply, and are not being suitable for high-volume production. For example, a previous helmet design is essentially a "vertical cylinder" that is difficult to manufacture and requires slow manual steps to assemble and weld.

Finally, previous solutions are not available in the quantities needed to treat all of the patients suffering from the COVID-19 pandemic. There are not enough domestic or foreign manufacturers of NIV helmets for a high demand situation.

SUMMARY

In a first aspect of the invention a NIV helmet includes one or more flat sheets of plastic arranged in an envelope and sealed around the periphery to form an airtight container. The helmet has an airtight collar that is configured to accommodate a patient's neck and form an airtight seal. An intake port is integrated into the helmet and receives pressurized air. An exhaust port is integrated into the helmet near the patient's mouth when the helmet is in use.

In a second aspect of the invention a NIV helmet is assembled from a flat sheet of plastic. Holes are cut in the sheet for an airtight collar and one or more ports. The collar is inserted into the hole for the collar. The one or more ports are inserted into the one or more holes for the ports. The collar and the one or more ports are welded to the sheet. The plastic sheet is folded on itself to form the helmet. The sides of the helmet are welded together to form an airtight helmet.

A third aspect of the invention teaches a method for treating a patient with respiratory distress. A patient's head is inserted into a noninvasive ventilation (NIV) helmet. The helmet is then sealed around the patient's head. The helmet is connected to a pressurized air supply. The pressurized air flows into the helmet creating a pressurized atmosphere.

BRIEF DESCRIPTION OF THE DRAWINGS

The accompanying drawings illustrate various non-limiting examples and innovative aspects of the ventilation helmet in accordance with the present description.

DETAILED DESCRIPTION

Figure 1:
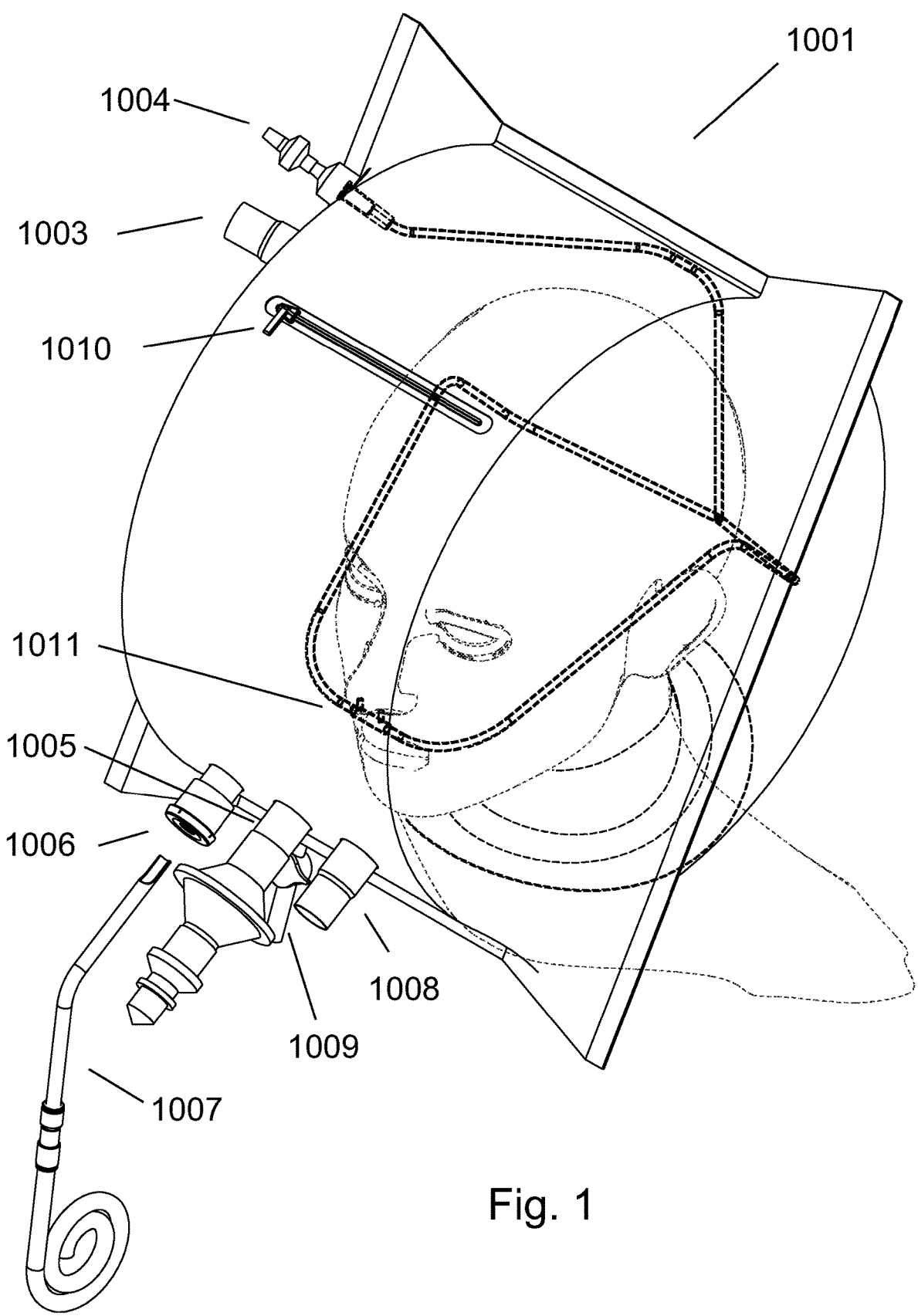
FIG. 1 is a perspective of a noninvasive ventilation helmet on a patient.
Figure 2:
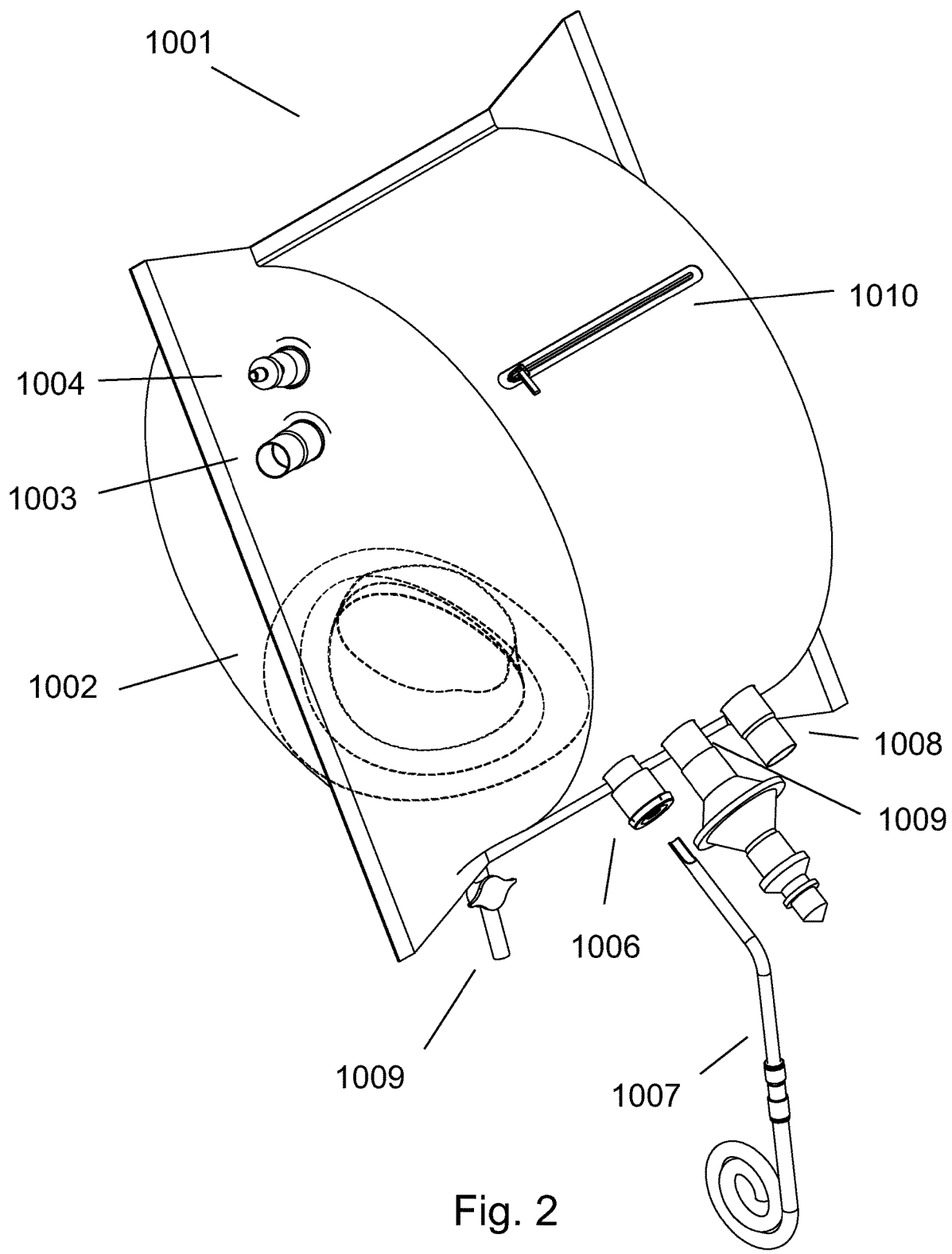
FIG. 2 is a perspective of a noninvasive ventilation helmet.
Figure 3:
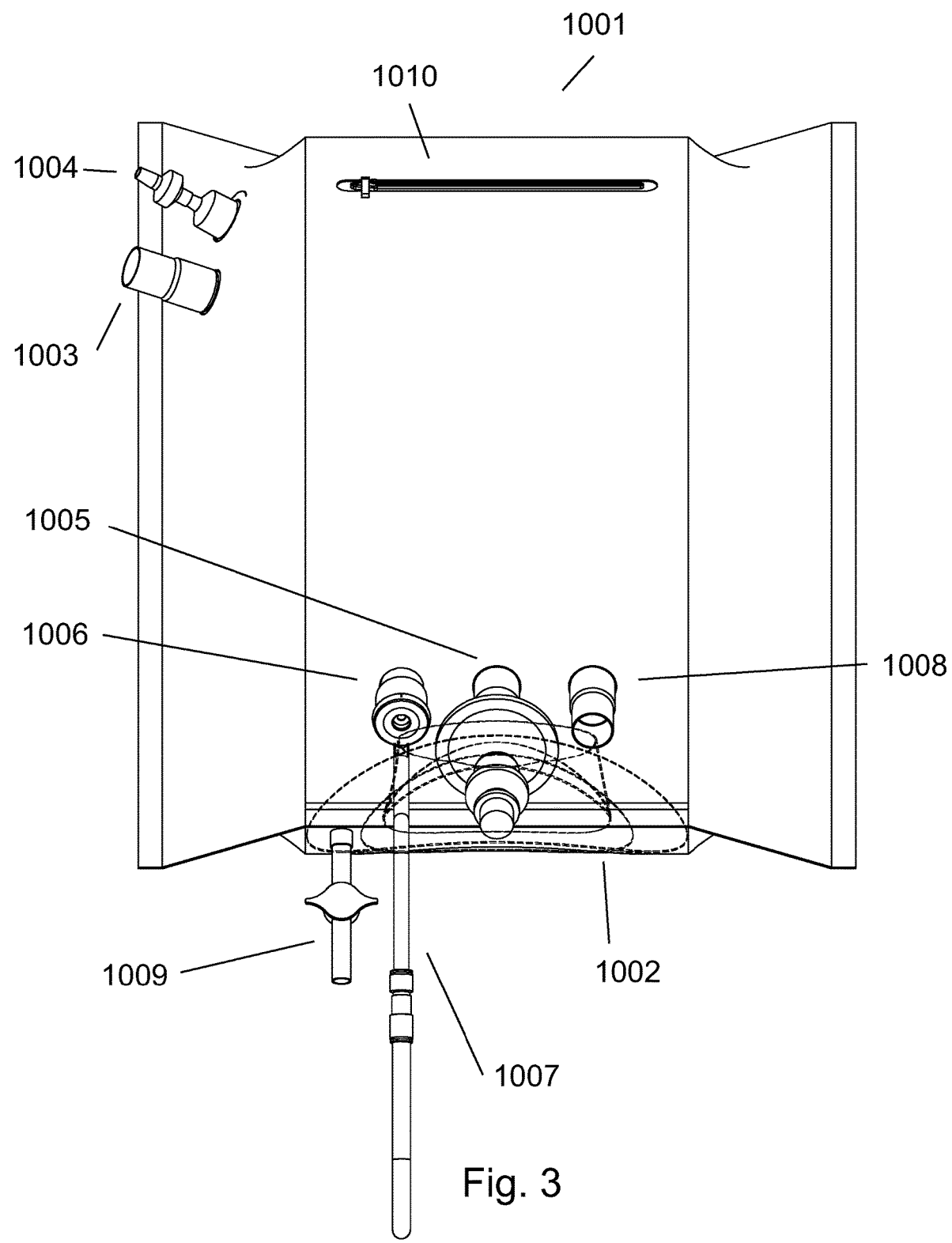
FIG. 3 is a front plan view of the noninvasive ventilation helmet.
Figure 4:
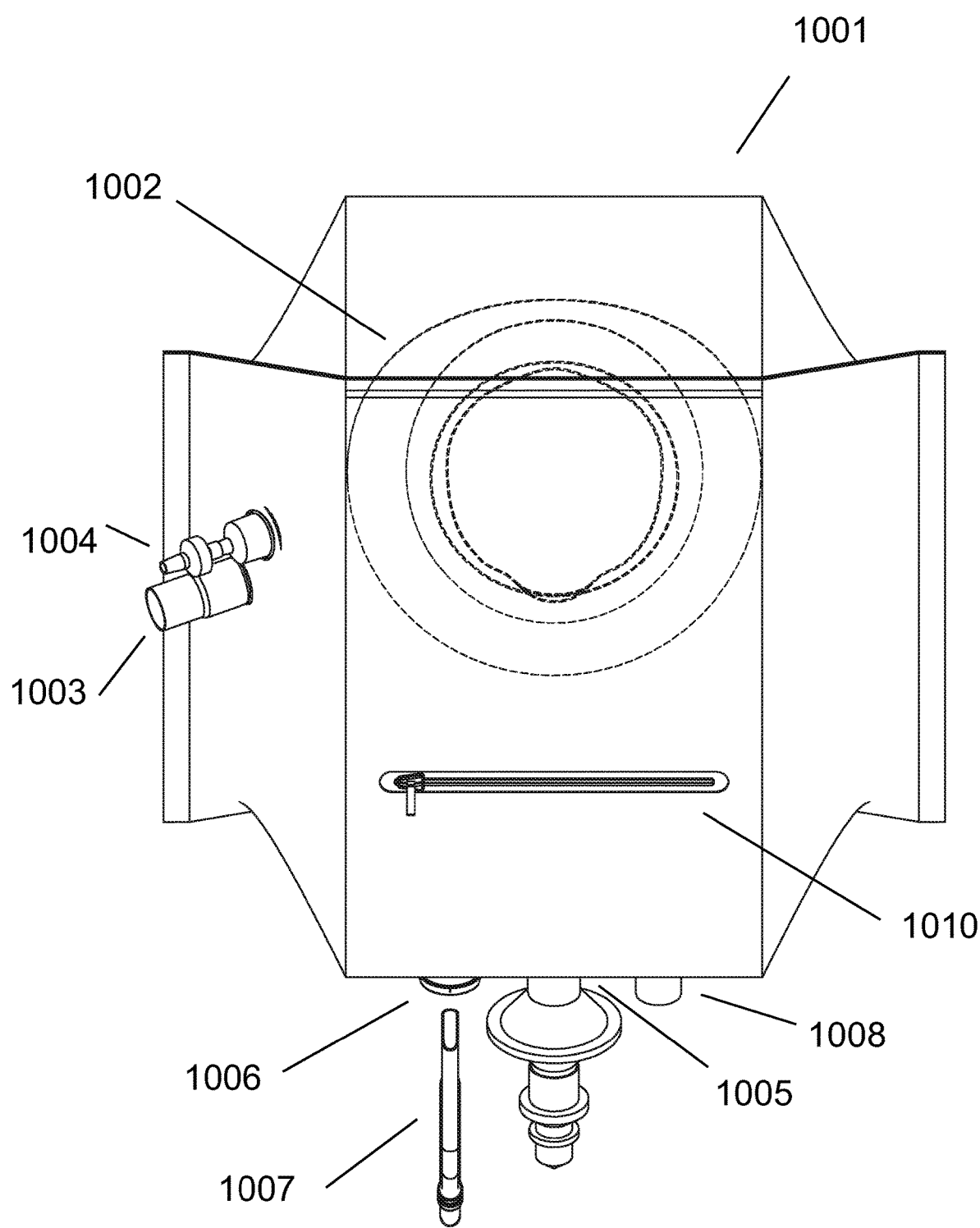
FIG. 4 is a top plan view of the noninvasive ventilation helmet.

The present disclosure describes a novel noninvasive ventilation helmet 1001. The disclosed noninvasive ventilation helmet or hood (NIV) 1001 is not limited to using a ventilator as its air supply. It is designed to use alternate air supplies which are widely available, including CPAP machines, PAPR blowers, oxygen venture valve or medical "wall air" (compressed air piped through the wall of hospitals) in addition to ventilators.

The current NIV helmet 1001 as shown in FIGS. 1-5 can use these alternate air supplies with a PEEP (positive end expiratory pressure) valve to provide positive pressure in the lungs. Medical studies have shown the effectiveness of such high-flow/elevated PEEP treatment to improve patient oxygenation of patients with serious respiratory issues. Houman Armirfarzan et al., Helmet CPAP: how an unfamiliar respiratory tool is moving into treatment options during COVID-19 in the US. 14:1-3 Therapeutic Advances in Respiratory Disease, Aug. 30, 2020. The same has been recently demonstrated by doctors treating COVID-19. Michael Harrison et al., Oxygen therapy via a noninvasive helmet: a COVID-19 novelty with potential post-pandemic uses, Respiratory Med. Case Rep. 32 (2021) 101369, Feb. 21, 2021. An integrated PEEP valve may be adjustable so that the healthcare provider can adjust their desired amount of PEEP, or it may be provided with a fixed or pre-set amount of PEEP to simplify decisions of caregivers who may be unfamiliar with proper settings or overwhelmed during a pandemic. The integrated PEEP valve may be adjustable so that the healthcare provider can adjust their desired amount of PEEP, or it may be provided with a fixed or pre-set amount of PEEP to simplify decisions of caregivers who may be unfamiliar with proper settings or overwhelmed during a pandemic.

Pre-set or range-limited adjustable PEEP values are important because too high of a PEEP value can damage the lungs, and also too high of pressure inside the helmet 1001 can exceed the helmet's 1001 pressure limit and lead to air leakage, especially around the neck.

"NIV" is an alternative to being on a ventilator. It involves using some sort of forced air (often with added oxygen) on the patient via a mask, helmet or similar device. NIV helmet 1001 systems do not necessarily "breathe" in and out the way a ventilator does. However, simply keeping the patients under forced air and positive pressure keeps the alveoli open and significantly improves oxygenation. It acts as a "splint" for their lungs, helping to keep the alveoli open.

Patients who are in more serious condition will still need to be on a ventilator. This NIV helmet 1001 disclosed herein can however help patients who are having difficulty with breathing but are not bad enough to require a ventilator. Many of these patients will recover while using the disclosed NIV. This type of product can keep patients from needing a ventilator. Bhakti Patel et al. Alternatives to Invasive Ventilation in the COVID-19 Pandemic. JAMA. 2020; 324(1):43-44. Jun. 4, 2020.

Previous NIV helmets were designed to help the patient, but were not designed to protect the caregivers. They do not seal perfectly and they allow exhaled (contaminated) air out into the room. NIV helmets 1001 involve forcing a high volume of air under pressure into the patient's lungs. The patient must exhale that air and it must be exhausted from the helmet. That exhaust air may contain the virus or other contaminants. Therefore, the exhaust air needs to be contained and filtered.

Previous NIV helmets do not adequately deal with the need to contain and filter the exhaust air. Previous products have poor quality seals that are not designed for this situation and do not provide for a means to feed and otherwise tend to the patient without exposing caregivers. The disclosed NIV helmet 1001 resolves these issues and was also designed for ease of manufacturing when compared to other designs (which are substantially a rigid vertical cylinder) requiring many more steps to seal all sides, including steps that are difficult to automate.

In an embodiment of the disclosure, the NIV helmet 1001 has a one piece "horizontal cylinder" design. In this embodiment, the entire NW helmet 1001 is one piece or multiple pieces that are bonded together. Previous designs have multiple components which must be assembled in the hospital and may have three main components: the main bubble, rigid center ring, and an airtight collar.

In an exemplary embodiment, a single clear plastic sheet in an open position may be manufactured with ports, neck openings and other access point described in further detail below. The sheet is then folded over and welded on the periphery to form the container or helmet 1001.

Figure 6:
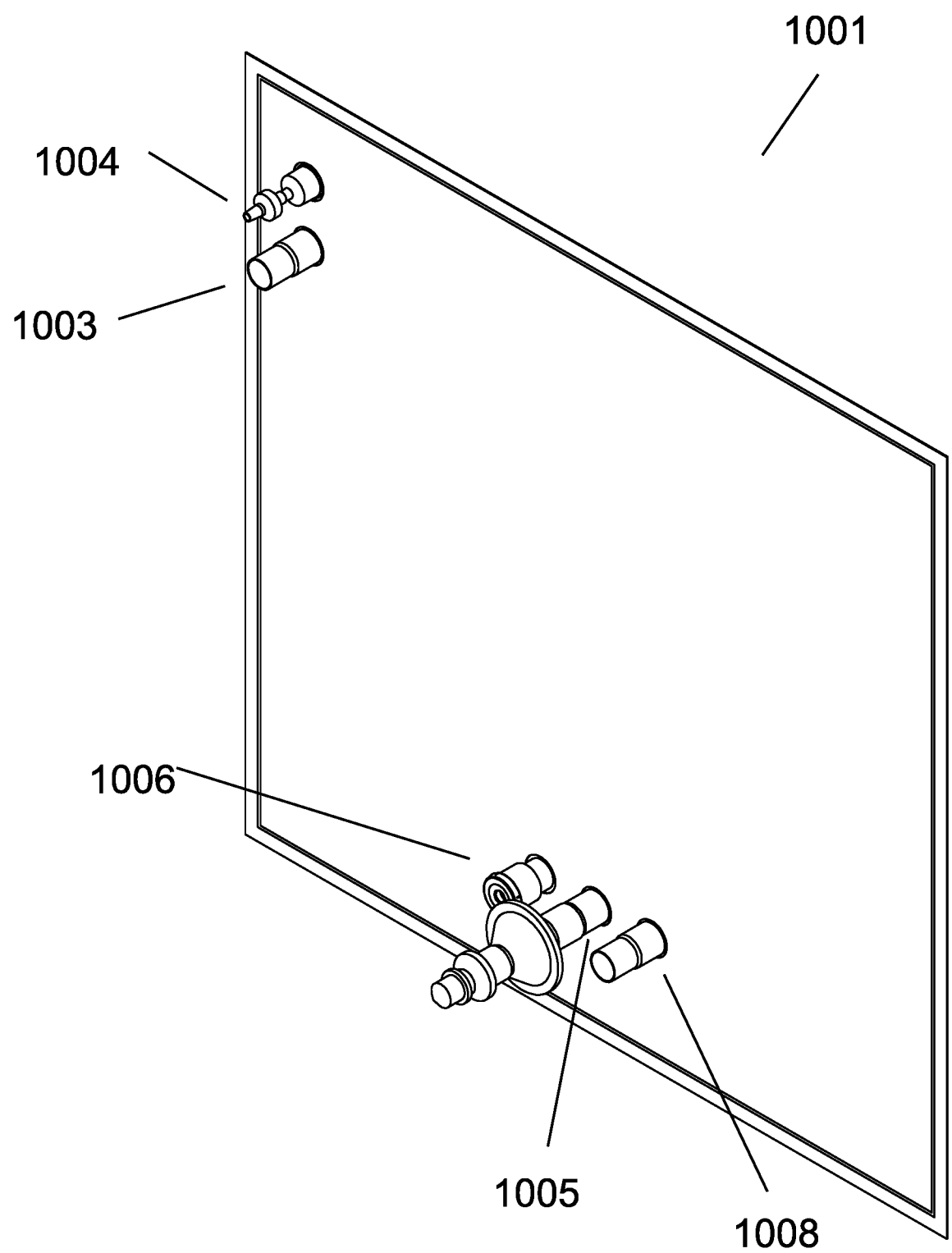
FIG. 6 is a perspective view of an uninflated noninvasive ventilation helmet.

This "in-the-flat" design of the helmet 1001 makes construction simple. In a first step the sheet in an open position has one or more holes punched in it for the ports and neck. In a second step the inserts (e.g., ports and zippers) and airtight collar 1002 are welded into their respective holes in the sheet. In a third step the sheet is folded preferably in half over onto itself. The resulting edges or periphery of the plastic sheet is then welded closed, creating a flat seam around the periphery. FIG. 6 is an example of the completed NIV helmet 1001, where the plastic sheet was rectangular in shape. This is a very fast and easy production process. This one-piece, rectangular shaped plastic sheet, folded-over-and-sealed design results in a "horizontal cylinder" appearance. In other embodiments, the plastic sheet may be in other shapes such that when it is folded and welded the resulting container or helmet 1001 has a spherical shape or other shape. For example, when in an uninflated state the helmet lies and has a substantially rectangular shape and in an inflated state the exemplary helmet 1001 shown in FIG. 2 forms a horizontal, cylindrical shape; i.e., with an interior void for receiving the patient's head that is in the shape of a horizontal cylinder. In other embodiments the helmet may have a circular shape when uninflated and lying flat and form a spherical interval void area or container of the helmet when inflated.

In some embodiments, a portion of the sheet that is positioned in front of the patient's face may also be coated in an anti-fog coating.

Figure 5:
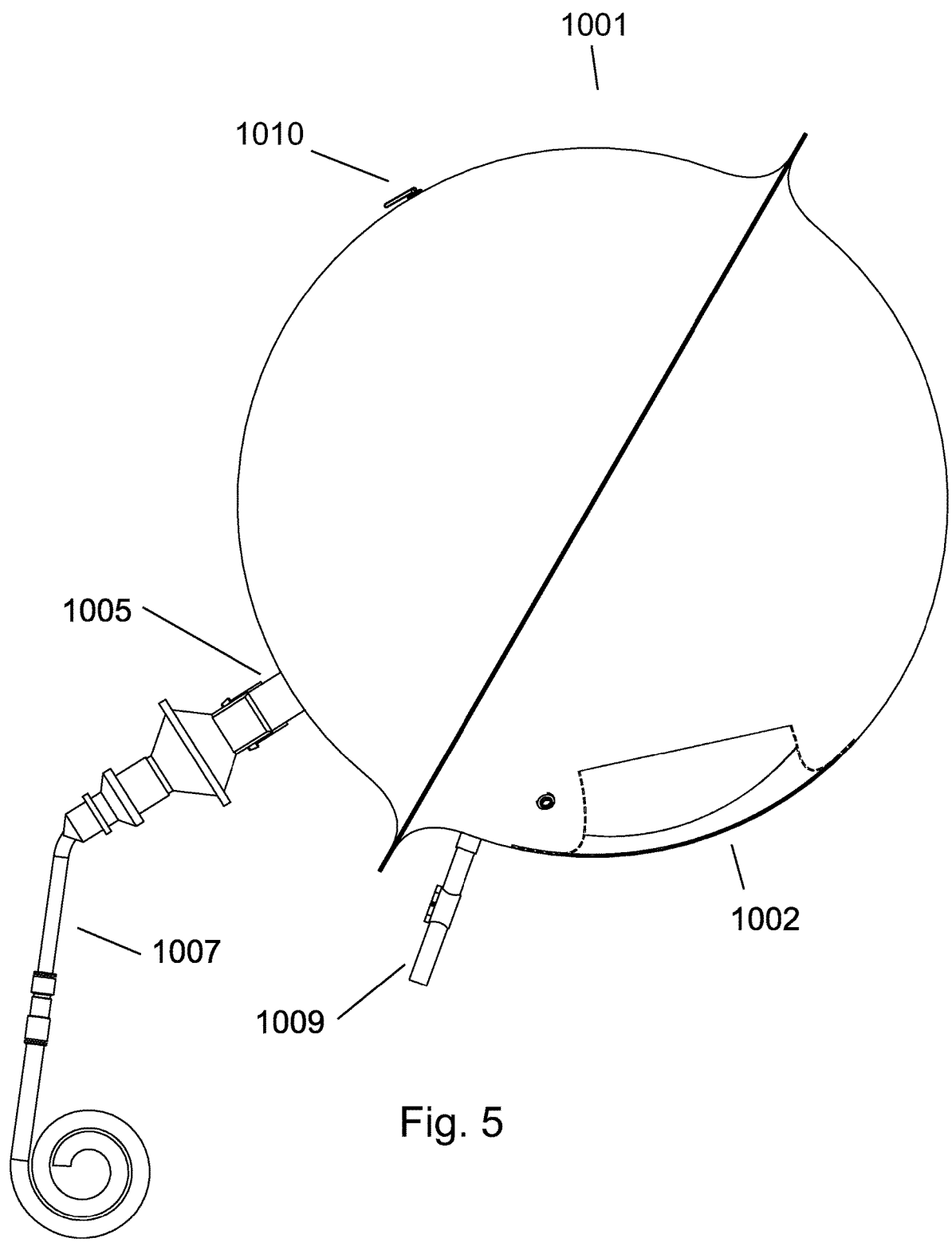
FIG. 5 is a side plan view of the noninvasive ventilation helmet.

FIG. 5 shows a side plan view with the main side seam visible. The seam can be arranged in many orientations including horizontal, angled, straight, etc. In an embodiment, the seam is oriented at an angle so the seam does not pass through the airtight collar 1002. By orienting the helmet's 1001 seam in front of or behind the airtight collar 1002 manufacturing is simplified and the reliability of the helmet 1001 is improved. The helmet 1001 may be seamed in a variety of way and orientations.

In an additional embodiment, the helmet may be made from multiple sheets or tube stock. For example, using tube stock the stock could be cut in sections and welded closed at the top and bottom so as to reduce the length and amount of welding needed. In other embodiments the helmet 1001 can be made of two or more sheets, for example, two sheets—a front half and back half—may be laid on top of one another and welded along the periphery to form the helmet 1001. As discussed above with respect to other embodiments, the plastic sheets may take a number of shape, e.g., circular to create spherical internal void area or rectangular to create a cylindrical internal void area. Other shapes such as oval or triangular and more sheet may be used as well.

The seams of the helmet 1001 can be welded using multiple methods. The welds can be formed using thermal impulse, adhesive, solvents, lasers, electric current, RF, or similar methods of welding. The helmet 1001 is configured to hold an atmosphere of at least 25 cm $H_2O$ and at least a temporary burst of 35 cm $H_2O$.

In an embodiment of the helmet 1001 gloves may be integrated into the helmet to improve access to the patient and the safety of the user. Gloves can be integrated into the helmet 1001 similar to a glovebox and welded to the helmet 1001 itself to form an airtight seal. This allows medical personal to reach into the helmet 1001 and manipulate other devices inside the helmet 1001 such as an oxygen cannula 1011 or a feeding tube 1007. The gloves can also be used in an examination. The gloves will naturally inflate and extend outside the helmet in an awkward manner. To prevent this, a seal such as a zipper separates the gloves from the helmet 1001 and prevents the gloves from being inflated when not in use. The gloves could also be rolled up and held in place with an integrated snap or tether.

An embodiment of the NIV helmet 1001 as shown in FIGS. 1-5 includes an airtight collar 1002, with a turtleneck-style airtight collar 1002. The airtight collar 1002 is preferably integrated and permanently attached to the helmet 1001. The airtight collar 1002 is preferably formed at an angle relative to the center of the helmet 1001 such that the head is located properly within the bubble, preventing the face from contacting the bubble and potentially suffocating the patient. The airtight collar 1002 is offset from the center and is positioned toward the rear of the helmet 1001. The airtight collar 1002 is made of an elastomeric material that can stretch to accommodate a patient's neck and head. The collar 1002 is configured to accommodate a patient's head. The collar 1002 is preferably capable of stretching to at least five times the collar's 1002 initial diameter. The collar 1002 may be made of a biocompatible material that can remain in contact with a patient's skin for an extended period of time. The seal may be made of a thermoplastic material such as santoprene or a similar material. The collar 1002 may be welded to the helmet 1001 by means of thermal sealing, radio frequency welding, ultrasonic welding, or through adhesive bonding.

Figure 9:
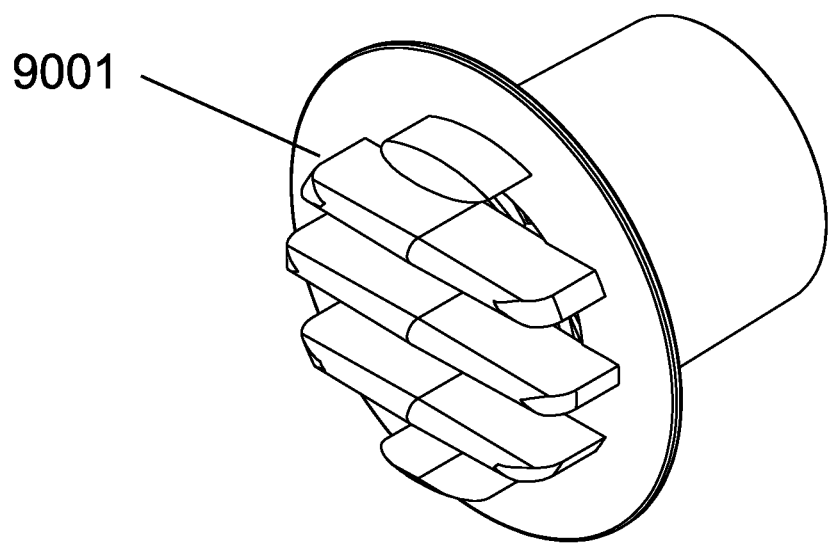
FIG. 9 is a perspective view of an intake port or an exhaust port.
Figure 10A:
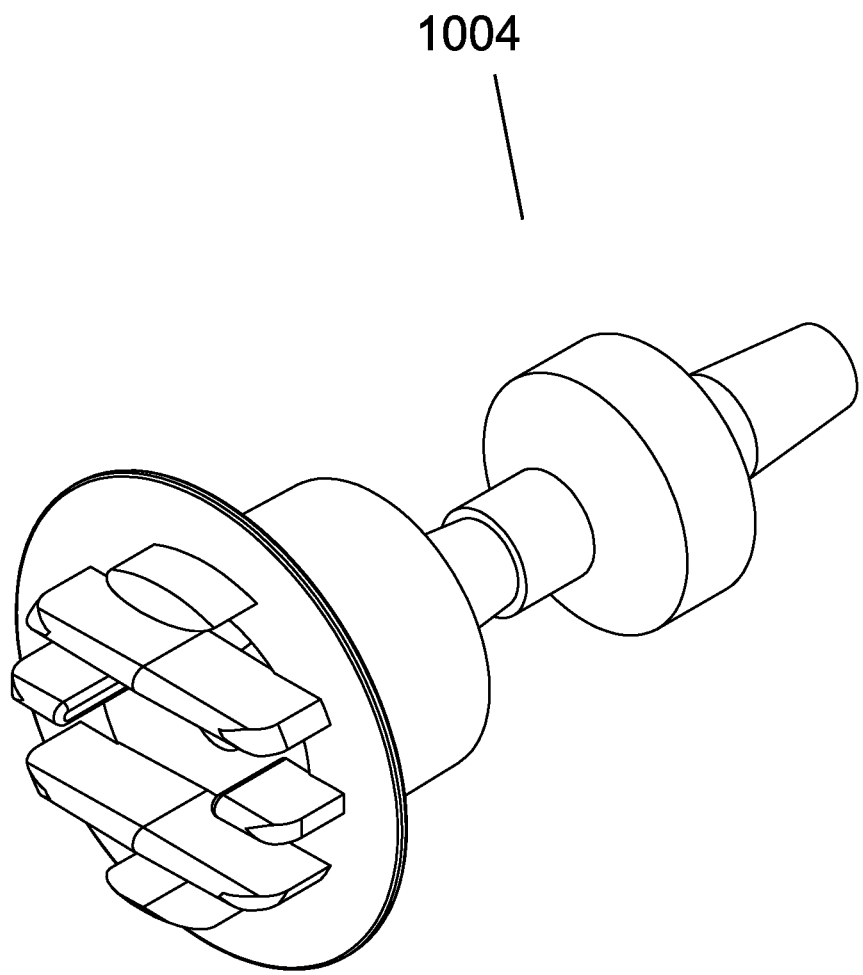
FIG. 10a is a perspective view of a supplemental oxygen port with check valve.
Figure 10B:
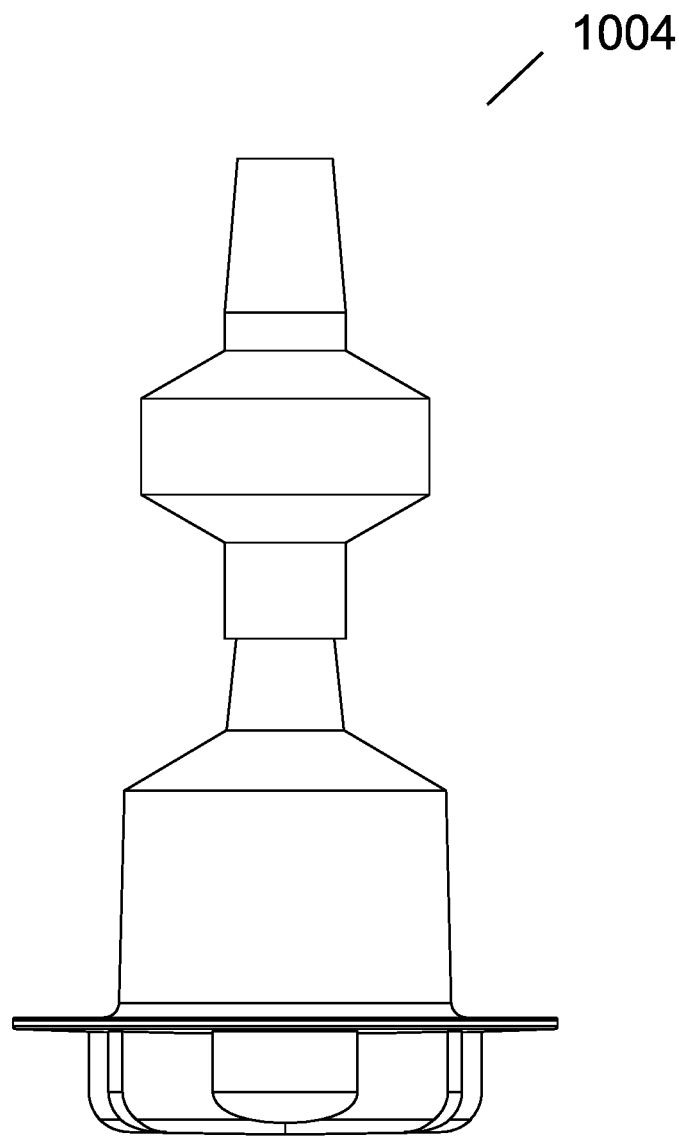
FIG. 10b is a plan view of a supplemental oxygen port with check valve.
Figure 10C:
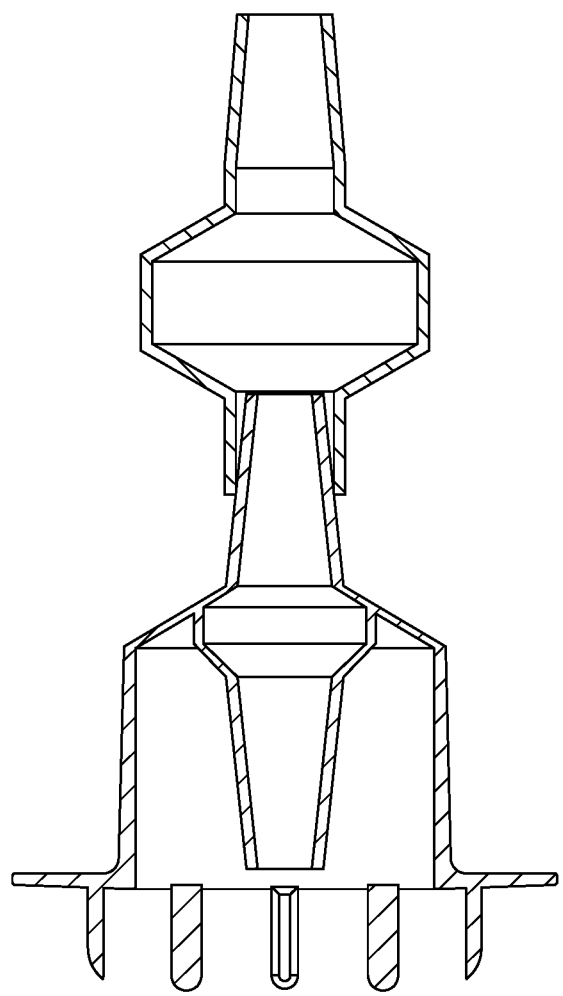
FIG. 10c is a cutaway view of a supplemental oxygen port with check valve.
Figure 11A:
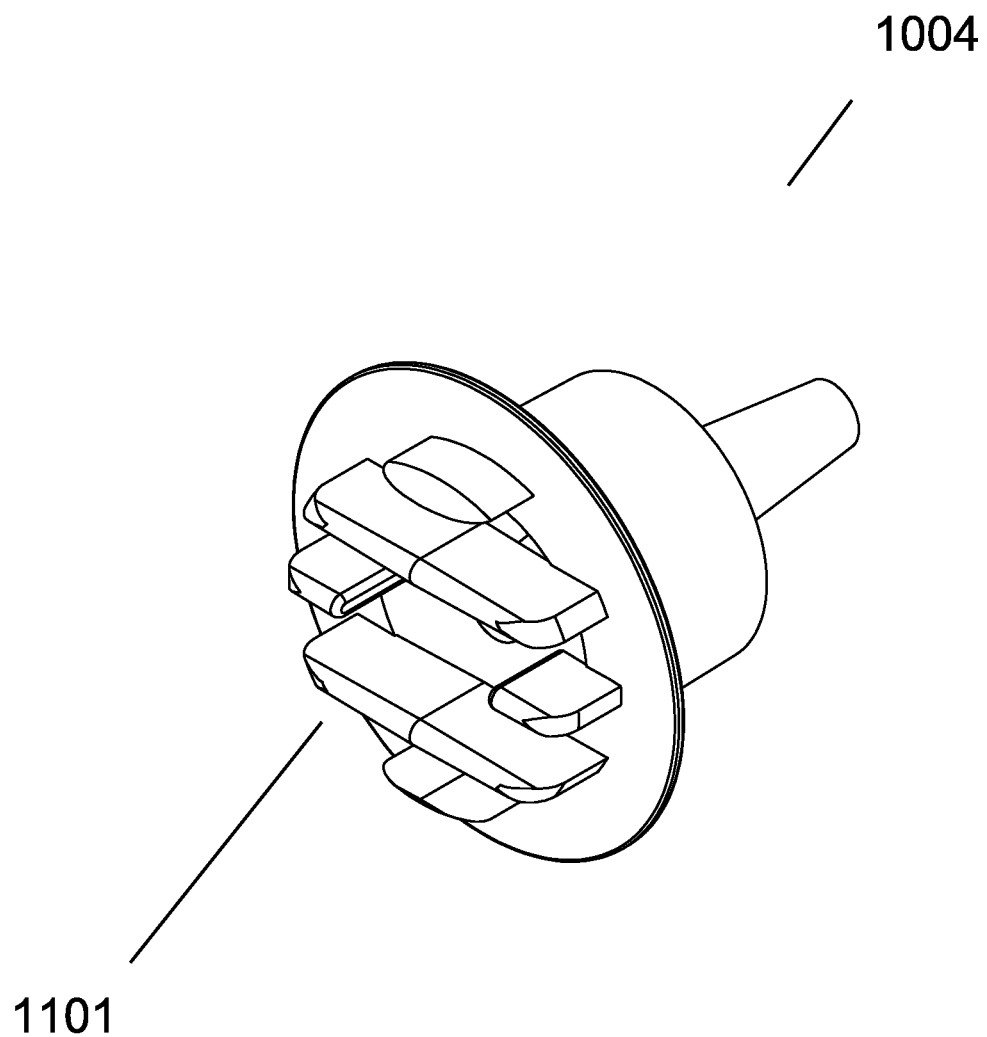
FIG. 11a is a perspective view of an alternate version of a supplemental oxygen port with check valve.
Figure 11B:
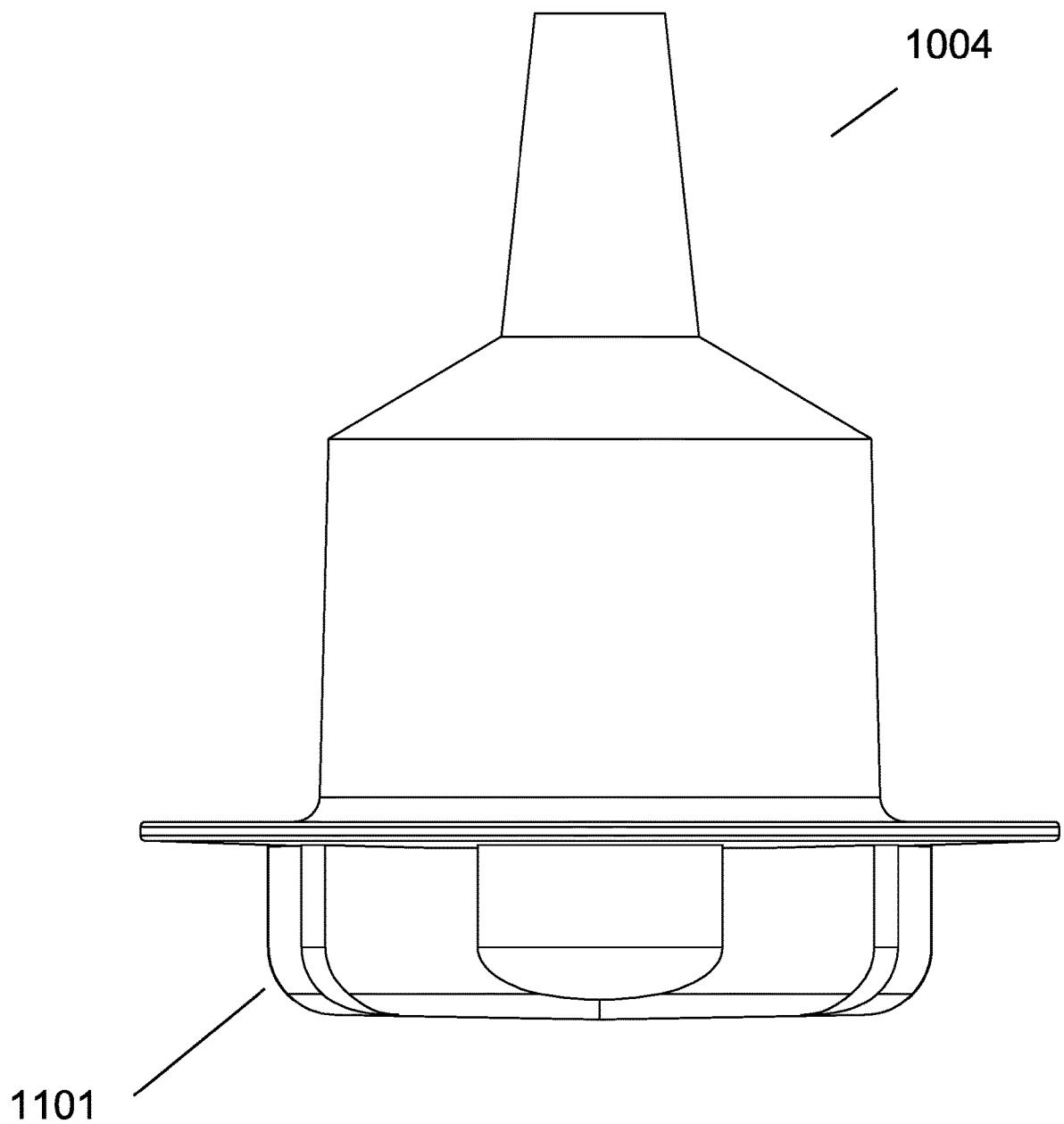
FIG. 11b is a plan view of a supplemental oxygen port with protective ribs.
Figure 11C:
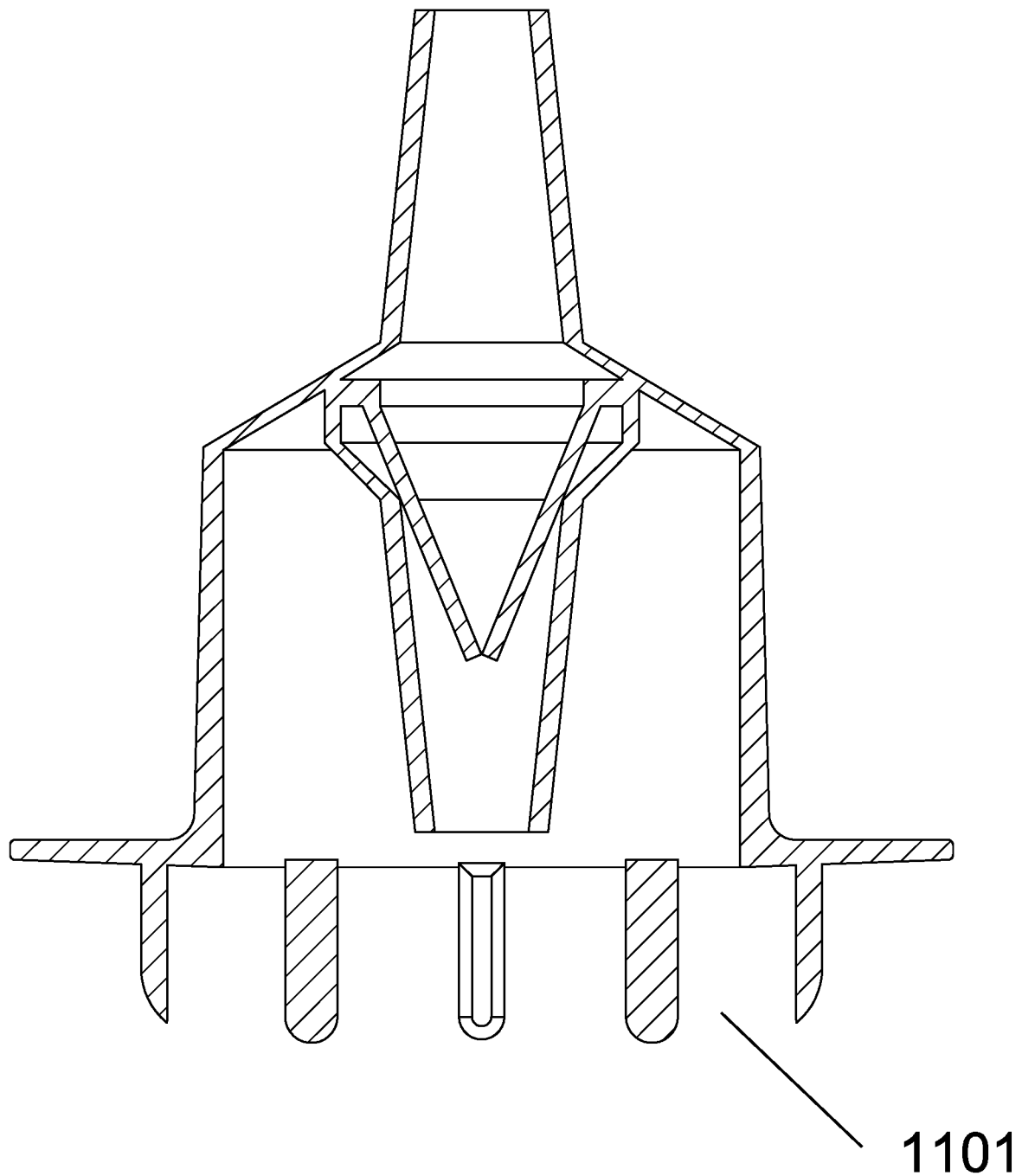
FIG. 11c is a cut away view of a supplemental oxygen port with protective ribs.

All of the ports in the helmet 1001 are integrated into the main bubble of the helmet 1001. The helmet 1001 has integrated check (one-way) valves on all ports to prevent air leakage when disconnected. An intake port 1003 and exhaust port 1005 may be two way ports. The helmet 1001 may include an intake port 1003. An exemplary embodiment of the intake port 1003 is shown in FIG. 9. The ports may be compatible with other 22 mm air tubing components. The ports are bonded to the helmet 1001 by thermal or RF welding, with an adhesive or by a similar process.

The atmosphere inside the helmet 1001 may be provided by a CPAP machine, PAPR, a ventilator, purified compressed air (known as "wall air" in hospitals) or similar air supply. This reduces the need for a ventilator as the air supply.

The helmet 1001 has an integrated barb for supplemental oxygen in a check valve so it is automatically sealed even if not used. FIGS. 10a-11c are exemplary embodiments of supplement oxygen ports. An accessory may be used to adapt the 22 mm intake port 1003 in the helmet 1001 to a "wall air" barbs an alternate air source. Additional embodiment may be made with more or less check valves 1102. In an additional embodiment, the inside of the intake port 1003 or oxygen port 1004 may be adapted to connect a nasal cannula 1011 to provide high flow nasal cannula 1011 therapy, which improves patient oxygenation. A patient's blood oxygen level may be monitored to determine if a patient needs additional oxygen. The port may also include protective ribs 1101 that prevent the port from being sealed if covered by the patient. If the blood oxygen level drops below 95% supplemental oxygen may be introduced to the patient in the helmet 1001.

An embodiment of the helmet 1001 includes an oxygen venturi valve, or can have an oxygen venturi valve integrated into the helmet 1001. The oxygen venturi valve may be connected to a 22 mm intake port 1003 that is already integrated into the helmet 1001. An oxygen venturi valve uses a stream of compressed gas, such as oxygen, to pull in a larger quantity of additional air from the room. The valve is engineered to pull in a specific amount of room air in proportion of the flow of oxygen supplied, and supply a relatively large amount of air which is enriched with a specific percentage of oxygen. Venturi valves are powered entirely by compressed gas and are portable. This will allow a simple oxygen tank to provide a sufficient flow of oxygenated room air to fill the helmet 1001 and provide a breathing environment for the patient.

The helmet 1001 may include an exhaust port 1005 located directly in front of a patient's mouth and nose. An exemplary embodiment of the exhaust port 1005 is shown in FIG. 9. This allows for the removal of $CO_2$, thus minimizing the re-breathing of $CO_2$, improves the patient's $O_2$ levels, and allows the helmet 1001 to function with lower airflow rates. The exhaust port 1005 may be equipped with a viral filter, HEPA filter or PEEP valve. The helmet 1001 may also include air inlet ports 1003 located as far away from the exhaust port 1005 as possible which also allows the helmet 1001 to function at a lower airflow rate and keep fresh oxygen in the helmet 1001.

As shown in FIGS. 1-5 the air inlet 1003 and exhaust ports 1005 integrated into the helmet 1001 have guards or ribbing 9001 which prevents the face or any internal objects from sealing the port. Anti-blockage guards on the valves ensure air can flow even if the patient's face or skin were to cover the valve opening. This prevents blockages and suffocation if the patient lays on their side or stomach and their skin presses on a port. An embodiment may also include an anti-asphyxiation valve 1008 to allow patients to breathe if their air supply is cut off.

The ports may be equipped with a sound reduction feature. The high air flow and pressurized compressed air and oxygen entering the helmet 1001 create a loud noise that may be discomforting for patients. Sound mufflers may be added on compressed air inlets, such as the oxygen connector. The sound mufflers are constructed from materials which are biocompatible and suitable for breathing gas and designed to ensure that no particulate matter is introduced into the patient's airway from the mufflers. Sound reduction baffles may also be installed on air inlets. The sound may be deflected by one or more baffles and is forced to travel an indirect path from the air entry to the patient's ears.

An embodiment of an air exhaust port 1005 includes a guard to prevent liquid or mucus from getting into a virus filter if the patient were to cough into it, which could block the filter or decrease its air flow rate. This may protect the patient from suffocation.

Figure 7:
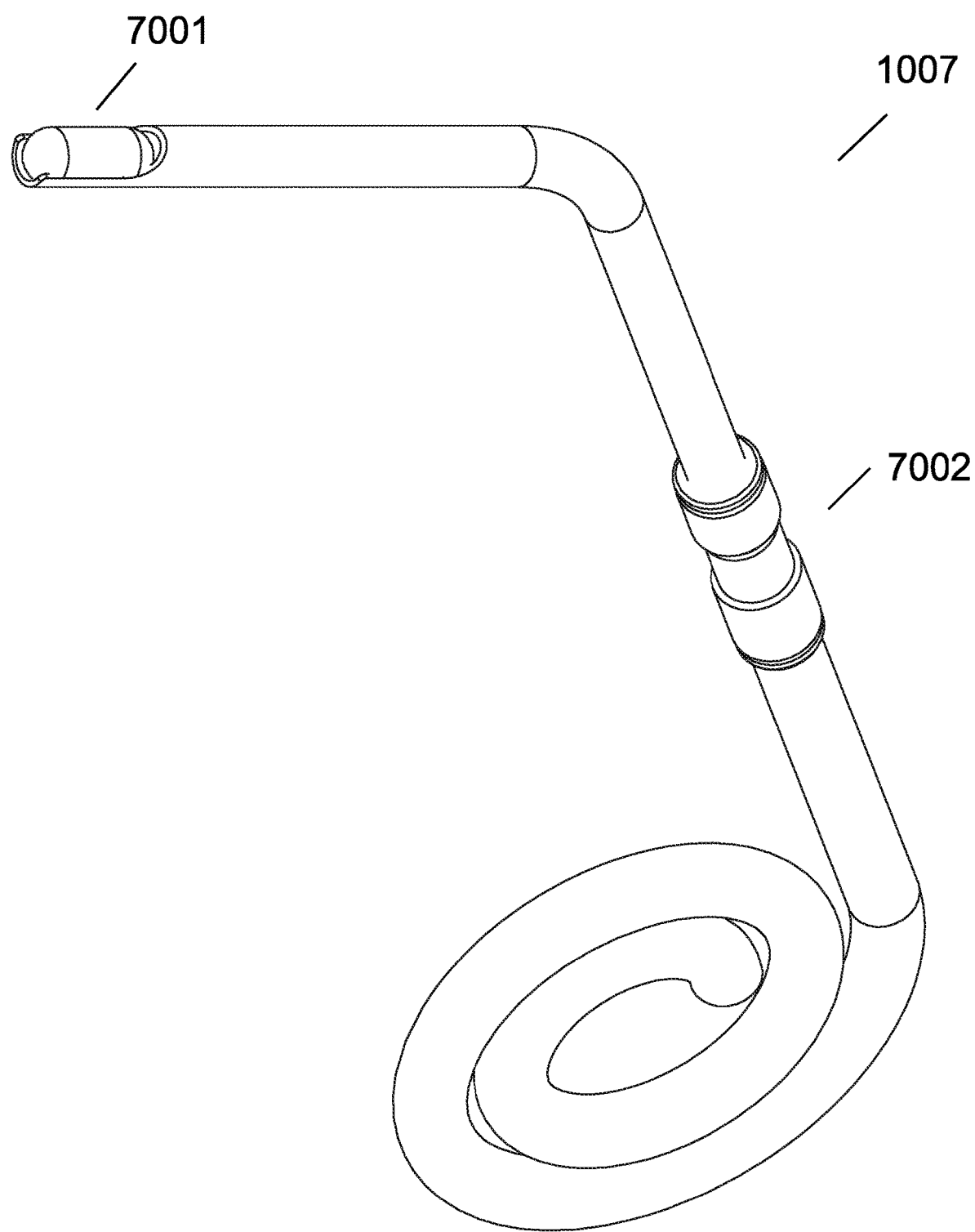
FIG. 7 is a perspective view of a feeding tube.
Figure 8A:
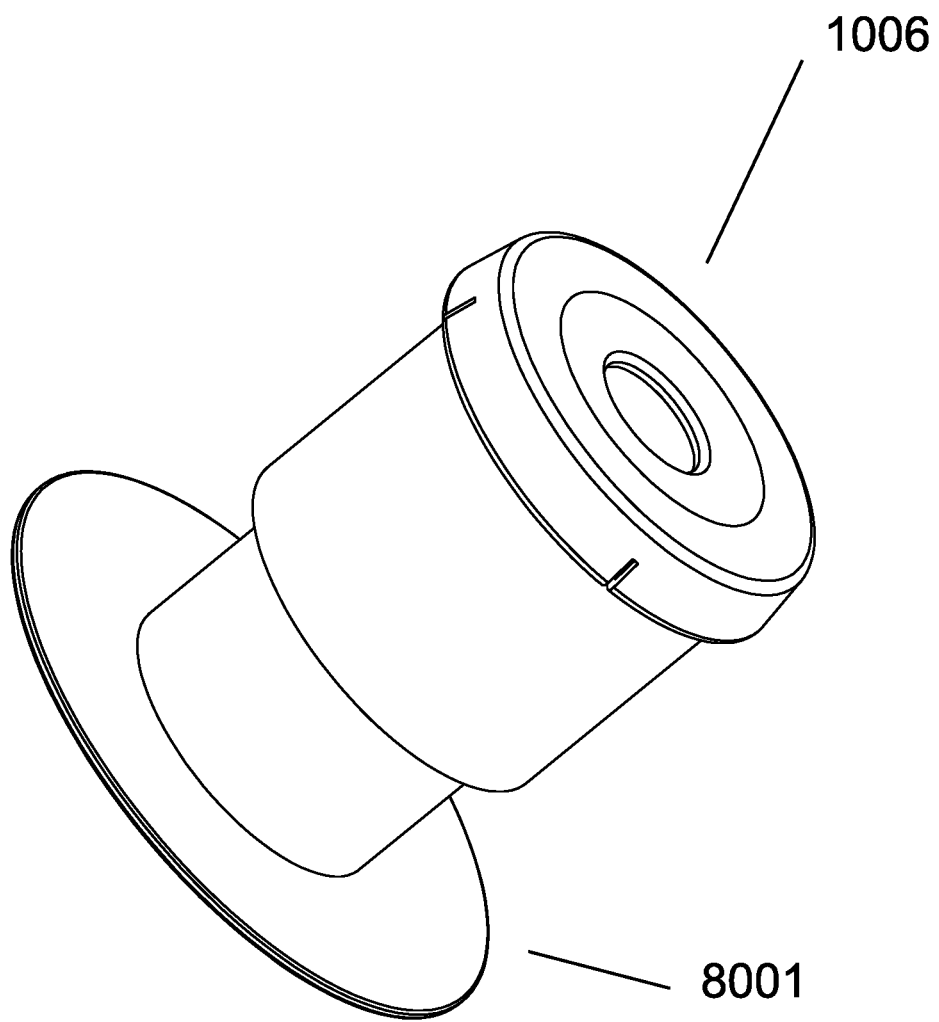
FIG. 8a is a perspective view of a feeding tube port.
Figure 8B:
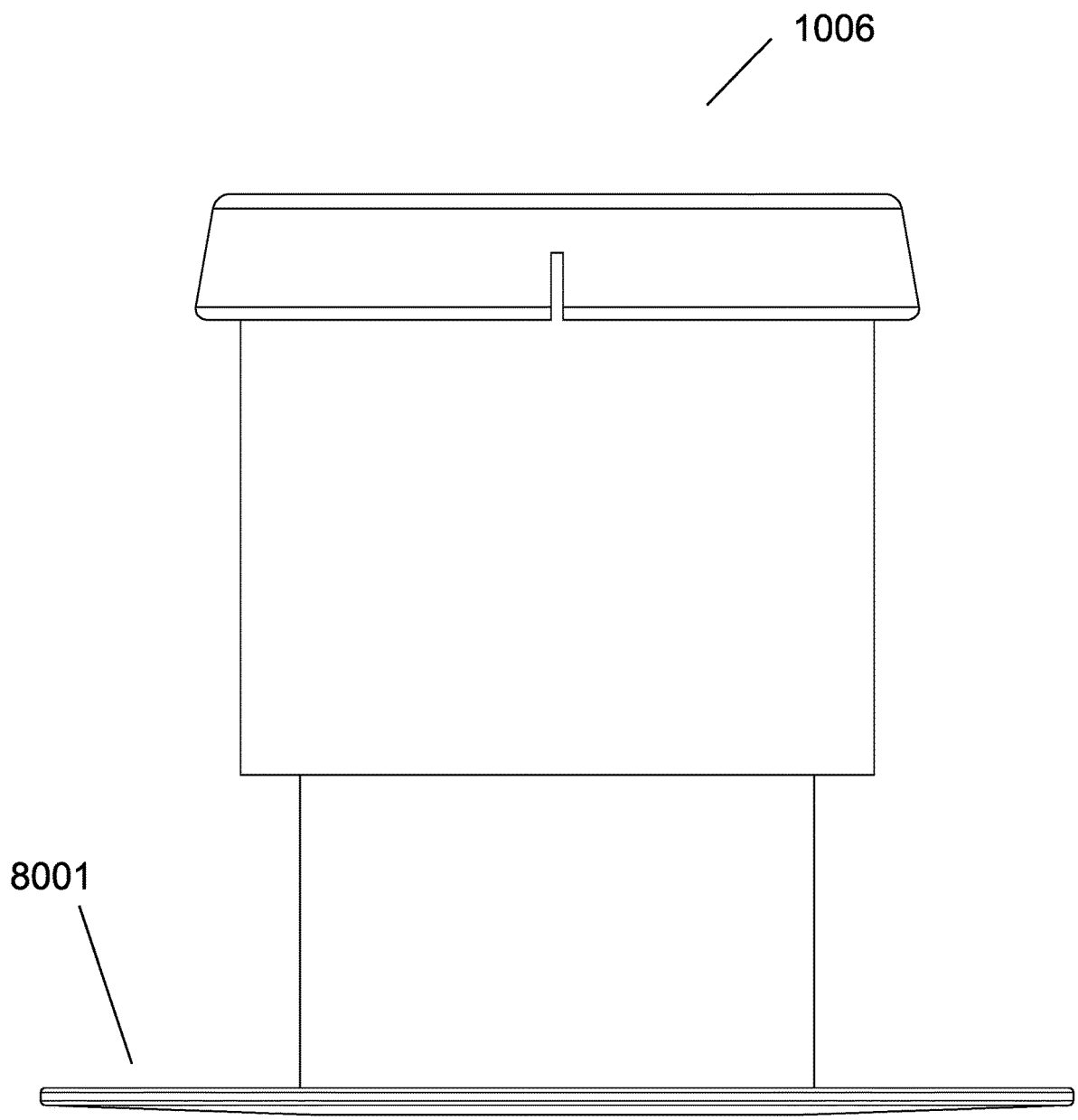
FIG. 8b is a plan view of a feeding tube port.
Figure 8C:
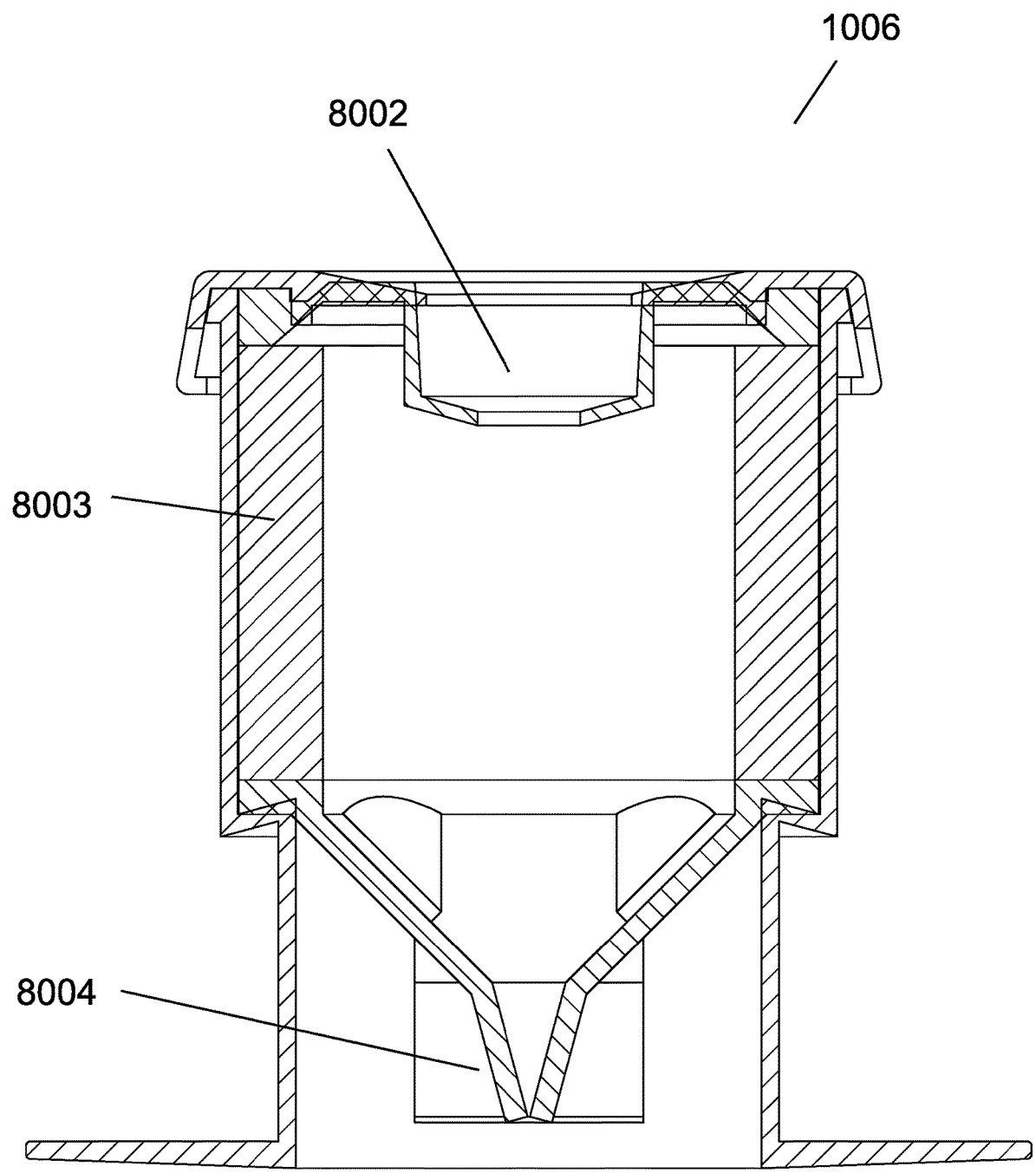
FIG. 8c is a cutaway view of a feeding tube port.
Figure 12:
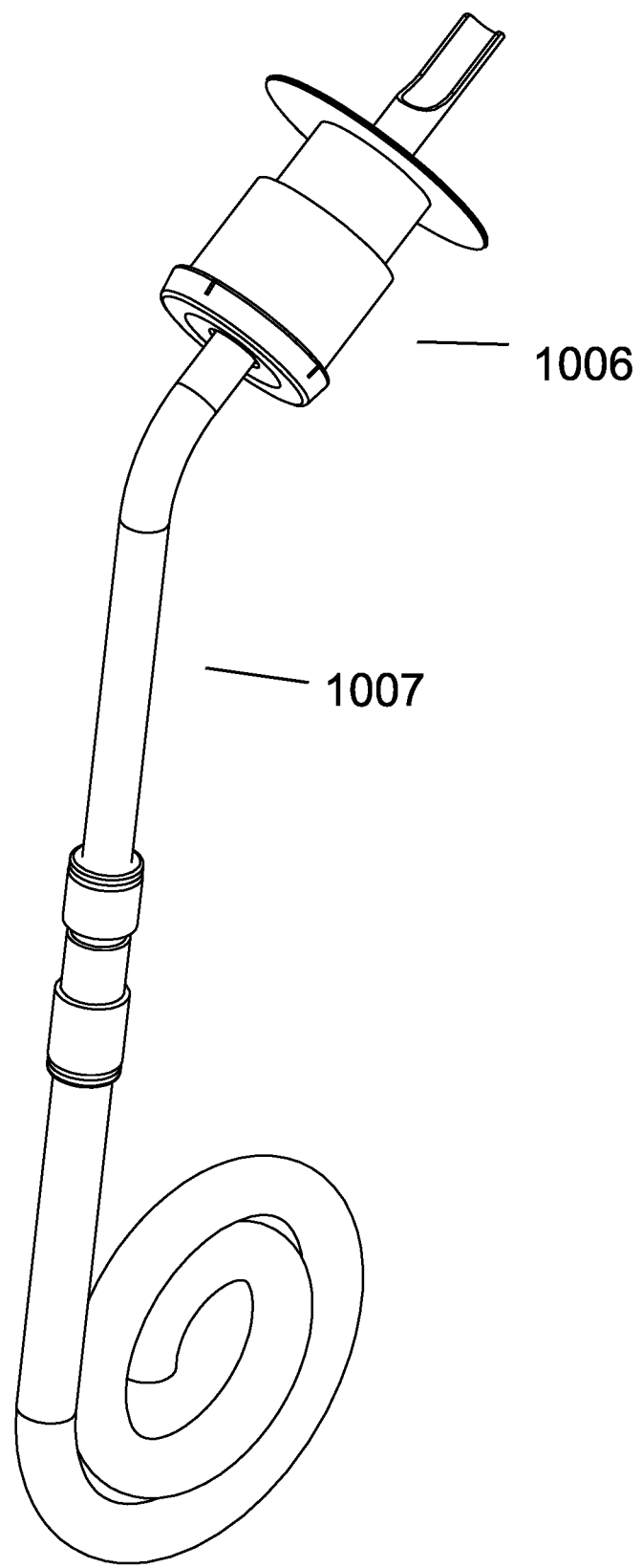
FIG. 12 is a perspective view of a feeding tube inserted into a feeding tube port.
Figure 13:
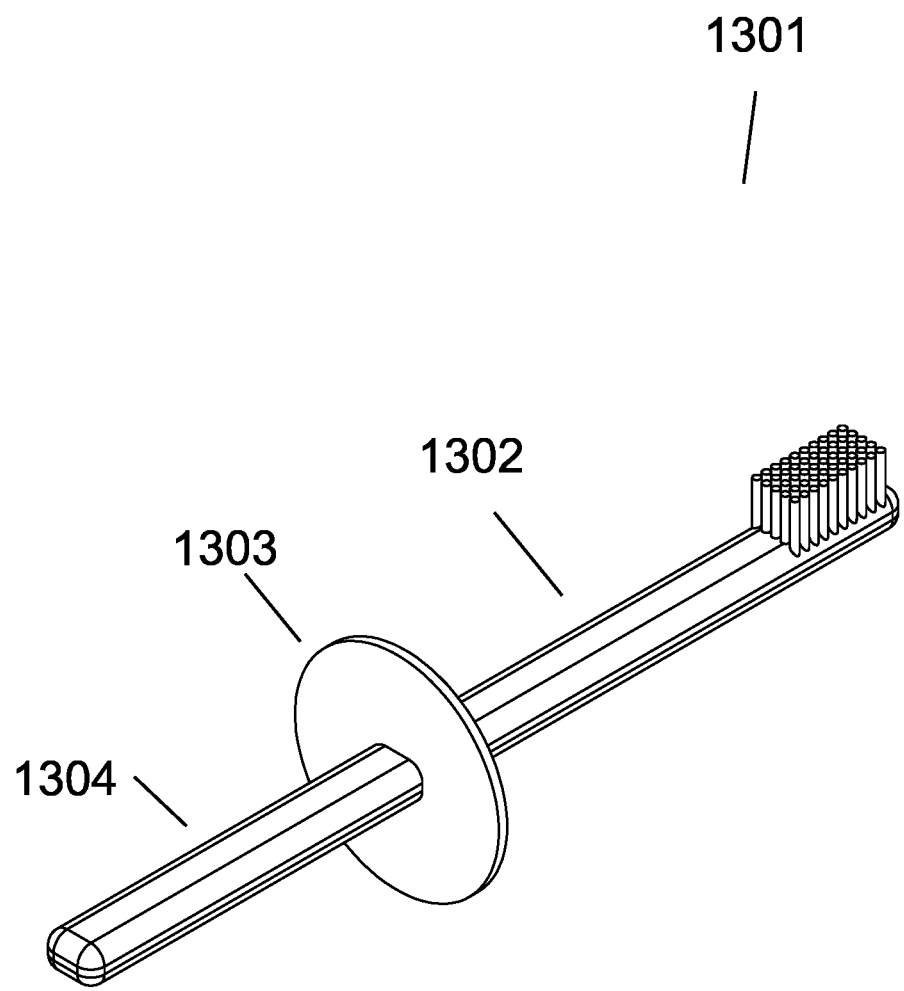
FIG. 13 is a perspective view of a toothbrush.

An embodiment of the helmet 1001 includes a feeding port 1006. An exemplary embodiment of the feeding port is shown in FIGS. 8a-8c. The feeding port 1006 is configured to accommodate a feeding tube 1007 that is inserted into the patient. An exemplary embodiment of the feeding tube is show in FIGS. 7 and 12. The feeding port 1006 includes a flange 8001 around the base that is welded to the helmet 1001. The exterior entrance includes a backup seal 8002 to prevent leakage before the feeding tube 1007 moves through the check valve 8004. A spacer 8003 ensures that the backup seal 8002 can seal around the feeding tube 1007 before it moves through the check valve 8004. The feeding port 1006 has an integrated trocar valve allowing insertion and removal of the feeding tube 1007 without air leakage. The feeding port 1006 may have an integrated check valve 8004. The feeding tube 1007 or straw may include an integrated check valve 7002 to prevent air from escaping through the feeding tube or straw 1007. Medication in the form of a pill 7001 can be inserted through the feeding port 1006 via a feeding tube, straw or spoon like device 1007.

An embodiment of the helmet 1001 includes a toothbrush 1301. A toothbrush configured to enter the helmet 1001 through the feeding port 1006 is used to clean the patient's teeth. The toothbrush and the feeding port 1006 are configured to maintain an airtight seal and prevent the spread of pathogens through the feeding port 1006. Additionally, a toothbrush 1301 may be integrated into the helmet 1001. A brush end 1302 is stored inside the helmet 1001 with a handle end 1304 extending through the helmet 1001. A flange 1303 is integrated around the middle of the toothbrush and welded to the helmet 1001 to maintain the airtight seal.

In an embodiment of the helmet 1001 includes a nozzle or similar device can be inserted through the feeding port 1006 for cleaning. During use a patient may soil the inside of the helmet 1001 and require cleaning. By inserting the nozzle through the feeding port 1006 the patient and the inside of the helmet 1001 can be cleaned without breaking the pressurized atmosphere or breaking the seal and potentially exposing other to contagious illnesses. The nozzle can spray water or a similar cleaning fluid.

An embodiment of the helmet 1001 includes a drain port with a valve 1009 to drain liquid spills such as food, cleaning fluid drink, etc. without removal of the bubble. The drain port 1009 is designed to connect directly to a sealed disposable waste container. The drain port 1009 may be used to remove the used cleaning fluid from inside the helmet 1001. The drain port 1009 with an attached waste container allows waste to be drained without allowing contaminated air to escape.

An embodiment of the helmet 1001 includes an $O_2$ or $CO_2$ sensor to monitor the patient. Carbon dioxide buildup in the helmet 1001 is dangerous and it can be difficult to continuously monitor the patient to ensure safety. An $O_2$ or $CO_2$ sensor may be integrated into the helmet 1001 or the exhaust port 1005. The $O_2$ or $CO_2$ sensor may be connected by wire or wirelessly to a hospital monitoring system. The $O_2$ or $CO_2$ sensor may wirelessly connect to medical staff communication devices, such as a cell phone or paging device, directly or via a mesh network. The $O_2$ or $CO_2$ sensor may contain an integrated audible alarm. If the oxygen or carbon dioxide level detected by the $O_2$ or $CO_2$ sensor meets a predetermined threshold an alert is triggered to notify medical staff.

An embodiment of the helmet 1001 includes an anti-asphyxiation valve 1008. The anti-asphyxiation valve 1008 is a pilot operated valve which is normally open when pilot pressure is below a setpoint. The normally open position is maintained by a spring. Pilot pressure comes from the pressure inside the helmet 1001. When pilot pressure is beyond a setpoint, the pilot pressure overcomes the spring and closes the anti-asphyxiation valve 1008. This closed state is the valve's typical state when the product is inflated and in use. If pilot pressure drops below a setpoint, the setpoint may be slightly above regular atmospheric pressure, indicating that the bag is deflated and no air is coming into the helmet 1001 the spring opens the anti-asphyxiation valve 1008, allowing free flow of air in and out of the helmet 1001.

Orienting patients in a prone position lying down provides significant relief when treating COVID-19. Accordingly, additional embodiments are adapted for use with patients laying in the prone position where they face downwards, or to the side. This embodiment may include alternate port locations to optimize airflow in relation to the orientation of the patient's head to the back or side, and/or additional or different anti-blockage mechanisms to prevent patient's face or skin from blocking the ports to ensure airflow.

An embodiment may have one or more of the side or seams use a resealable mechanism 1010 such as an interlocking groove and ridge or an airtight zipper, allowing the helmet 1001 to open and provide complete access to the patient if needed. The opening for the resealable mechanism 1010 is positioned to allow medical personal to quickly open the helmet and intubate the patient or perform another operation in an emergency situation.

An embodiment has integrated snaps and under-arm tethers (tethers not shown) to hold the helmet 1001 down. The helmet 1001 has a tendency to push the patient's head out under pressure and to ride up on the neck and the tethers secure the patient within the helmet 1001. The helmet 1001 may use alternate means of holding the unit on the patient.

An embodiment has a humidification module configured to humidify supplied air. Humidification is a requirement for air used in a ventilation application as standard oxygen and air is dry. Without humidification the dry air may lead to airway inflammation and difficulty breathing. The humidification module may be integrated into the helmet 1001 or an external device. The humidification module may be an integrated feature of the helmet 1001, with the water columns being formed directly into the plastic enclosure of the helmet 1001. The humidification module may be an enclosed column of water or liquid solution in which air is bubbled through on its way to the patient. Air or gas would be introduced to the humidification system at the bottom of the water column, and the air would exit into the patient's enclosure at the top of the water column. An additional embodiment could include multiple sequential water columns side by side so that the air must pass through multiple water columns and collect additional humidity prior to reaching the patient.

Although the foregoing description has been made with respect to preferred embodiments of the present invention it will be understood by those skilled in the art that many variations and alterations are possible. Some of these variations have been discussed above and others will be apparent to those skilled in the art.

What is claimed is:

1. A ventilation helmet comprising:
   one or more flat sheets of plastic having a rectangle, circle, oval or triangle shape, a seam formed around a periphery of the sheets to form a container, and is configured to change into a different shape when inflated;
   an airtight collar integrated into the container and configured to accommodate a patient's neck and form an airtight seal;
   an intake port configured to receive pressurized air and discharge air directly into the container, wherein the intake port has an interior end inside the helmet and an exterior end outside the helmet;
   an exhaust port located near a patient's mouth when the helmet is in use and the exhaust port is equipped with a filter configured to prevent the release of pathogens from within the container; and a protrusion disposed at the interior end of the intake port, the protrusion extends beyond the intake port into the interior of the helmet and the protrusion extends over the opening of the intake port, and the protrusion is configured to prevent blockage of the intake port by the patient.

2. The helmet of claim 1, wherein a resealable mechanism is integrated into the helmet.

3. The helmet of claim 2, wherein the resealable mechanism is an interlocking groove and ridge or an airtight zipper.

4. The helmet of claim 1, wherein the collar is tilted at an angle configured to prevent a patient's face from rubbing on the helmet.

5. The helmet of claim 1, wherein the collar is made of an elastomeric material configured to stretch around the patient's head and neck, form an airtight seal with the patient's neck and not irritate the patient's skin.

6. The helmet of claim 1, wherein the seam of the helmet is formed using thermal impulse, solvent, adhesive, laser, electric current or RF welding.

7. The helmet of claim 1, wherein a venturi valve is integrated into the helmet and configured to receive a pressurized air supply.

8. The helmet of claim 7, wherein the venturi valve provides a mixture of pressurized air and air from outside the container into the container.

9. The helmet of claim 1, wherein a venturi valve is integrated into the intake port and configured to receive a pressurized air supply.

10. The helmet of claim 1, wherein the protrusion is supported by the interior end of the intake port.

11. The helmet of claim 1, wherein the collar is located closer to a rear of the helmet than a front of the helmet.

12. A ventilation helmet comprising:
a container formed from flexible plastic having a base portion and side portion, wherein the container has at least two states, a first uninflated state having a rectangle, circle, oval or triangle shape wherein the container is collapsed to lie flat and a second inflated state having a different shape than the first uninflated state wherein the flexible plastic defines an interior void region configured to fit over a patient's head;
an airtight collar integrated into the base portion of the container and adapted to form an airtight seal around a patient's neck;
an intake port configured to receive pressurized air and discharge air directly into the container, wherein the intake port has an interior end inside the helmet and an exterior end outside the helmet;
an exhaust port disposed in the side portion of the container adjacent the base portion and the exhaust port is equipped with a filter configured to prevent the release of pathogens from within the container, whereby the exhaust port located near a patient's mouth when the helmet is in use; and
a protrusion disposed at the interior end of the intake port, the protrusion extends beyond the intake port into the interior of the helmet, the protrusion extends over the opening of the intake port, and the protrusion is configured to prevent blockage of the intake port by the patient.

13. The ventilation helmet of claim 12 wherein, the container is formed from the flexible plastic comprising one or more flat sheets of plastic bonded together along the periphery to form the container.

14. The ventilation helmet of claim 12 wherein, the container formed from the flexible plastic comprises a tubular shape bonded together along the periphery to form the container.

15. The ventilation helmet of claim 12 wherein, the container formed from the flexible plastic comprises a single sheet of plastic folded over on itself and bonded along the periphery.

16. The ventilation helmet of claim 12, wherein the protrusion is supported by the interior end of the intake port.

17. The helmet of claim 12, wherein a venturi valve is integrated into the helmet and configured to receive a pressurized air supply.

18. The helmet of claim 17, wherein the venturi valve provides a mixture of pressurized air and air from outside the container into the container.

19. The helmet of claim 12, wherein the collar is located closer to a rear of the container than a front of the container.

* * * * *